US00PP11284P

United States Patent [19]

Dümmen

[11] Patent Number: Plant 11,284

[45] Date of Patent: Mar. 14, 2000

[54] NEW GUINEA IMPATIENS PLANT NAMED 'DUERIHOPI'

[75] Inventor: Marga Dümmen, Rheinberg, Germany

[73] Assignee: Dummen Jungpflanzenkulturen, Rheinberg, Germany

[21] Appl. No.: 09/038,771

[22] Filed: Mar. 11, 1998

[51] Int. Cl.[7] ..... A01H 5/00

[52] U.S. Cl. ..... Plt./318

[58] Field of Search ..... Plt./317, 318

[56] References Cited

U.S. PATENT DOCUMENTS

P.P. 8,264 6/1993 Dehan ..... Plt./318

*Primary Examiner*—Howard J. Locker
*Attorney, Agent, or Firm*—C. A. Whealy

[57] ABSTRACT

A new and distinct variety of New Guinea Impatiens plant named 'Duerihopi', characterized by its dark hot pink petal color; freely flowering and branching plant habit; and dark green, glossy and non-variegated foliage.

1 Drawing Sheet

BACKGROUND OF THE INVENTION

The present invention relates to a new and distinct variety of New Guinea Impatiens plant, botanically known as *Impatiens hawkeri*, and hereinafter referred to by the name 'Duerihopi'.

The new variety is a product of a planned breeding program conducted by the inventor in Rheinberg, Germany. The objective of the breeding program is to develop New Guinea Impatiens that are freely branching; compact; early flowering; and that have desirable flower and leaf colors.

The new cultivar originated from a cross made by the inventor of the variety Grenada (disclosed in U.S. Plant Pat. No. 9,343) as the male, or pollen, parent with the variety Dark Delias (disclosed in U.S. Plant Pat. No. 9,139) as the female, or seed, parent.

'Duerihopi' was discovered and selected in 1995 by the inventor as a single flowering plant within the progeny of the stated cross in a controlled environment in Rheinberg, Germany.

Asexual reproduction of the new variety by terminal cuttings taken at Rheinberg, Germany, has shown that the unique features of this new variety are stable and reproduced true to type in successive generations of asexual reproduction.

BRIEF SUMMARY OF THE INVENTION

The following traits have been repeatedly observed and are determined to be the unique characteristics of 'Duerihopi'. These characteristics in combination distinguish 'Duerihopi' aw a new and distinct variety:

1. Dark hot pink petal color.
2. Freely flowering.
3. Dense and bush plant habit.
4. Freely and basally branching plant habit.
5. Dark green, glossy and non-variegated foliage.

The new variety can be compared to the commercial cultivar Dark Delias. However, in side-by-side comparisons conducted by the inventor in Rheinberg, Germany, plants of the new variety differed from plants of 'Dark Delias', in the following characteristics:

1. Plants of the new variety have a faster growth rate than plants of 'Dark Delias'.

2. Plants of the new variety are more freely branching than plants of 'Dark Delias'.

3. Plants of the new variety have shorter internodes than plants of 'Dark Delias'.

4. Plants of the new variety are more floriferous than plants of 'Dark Delias'.

5. Plants of the new variety have smaller flowers than plants of 'Dark Delias'.

6. Flower petals of plants of the new variety are slightly darker in color than flower petals of plants of 'Dark Delias'.

BRIEF DESCRIPTION OF THE PHOTOGRAPH

The accompanying colored photograph illustrates the overall appearance of the new variety, showing the colors as true as it is reasonably possible to obtain in colored reproductions of this type. The photograph comprises a side perspective view of a typical plants of 'Duerihopi' grown in a 12-cm container. Flower and foliage colors may appear different from the actual colors due to light reflectance.

DETAILED BOTANICAL DESCRIPTION

Plants of 'Duerihopi' have not been observed under all possible environmental conditions. The phenotype may vary somewhat with variations in environment such as temperature, daylength and light intensity, without, however, any variance in genotype. The following observations and measurements describe plants grown in 12-cm containers during the spring in Rheinberg, Germany, under commercial practice in a glass-covered greenhouse with day and night temperatures about 18° C. and light levels about 45 thousand lux.

In the following description, color references are made to The Royal Horticultural Society Colour Chart except where general terms of ordinary dictionary significance are used.

Botanical classification: *Impatiens hawkeri* 'Duerihopi'.

Parentage:

*Male, or pollen, parent.*—*Impatiens hawkeri* 'Grenada'.

*Female, or seed, parent.*—*Impatiens hawkeri* 'Dark Delias'.

Propagation:

*Type cutting.*—Terminal cuttings.

*Time to initiate roots.*—Summer: About 10 days at 22° C. Winter: About 12 days at 22° C.

*Time to develop roots.*—Summer: About 21 days at 22° C. Winter: About 26 days at 22° C.

*Rooting habit.*—Freely branching.

Plant description:

*General appearance.*—Rounded; dense and bushy; very freely and basally branching; upright and spreading; rapid growth rate and moderate vigor; suitable for 10 to 16-cm pots.

*Plant height.*—About 17 cm from soil level to top of plant plane.

*Lateral branches.*—Length: About 7.5 cm. Diameter: About 6.6 mm. Internode length: About 2.25 cm. Color: 136A.

*Foliage description.*—Quantity of leaves per lateral branch: About 33. Shape: Elliptic with acuminate tip and attenuate base. Length: About 7.4 cm. Width: About 2.8 cm. Texture: Smooth, glossy and glabrous. Margin: Serrulate. Color: Young foliage, upper surface: 133A. Young foliage, lower surface: 197B. Mature foliage, upper surface: 131A. Mature foliage, lower surface: 197A. Veins, upper surface: 195A. Veins, lower surface: 187C. Petiole: Length: About 2.1 cm. Diameter: About 2.5 mm. Color: 133A.

Flower description:

*Flowering habit.*—Freely flowering.

*Natural flowering season.*—Year-round. Plants flower about 8 weeks after planting.

*Flowers borne.*—Flower buds develop in apical leaf axils. Open flowers are displayed above the foliage.

*Quantity of inflorescences.*—Freely flowering, usually about 38 buds and flowers per plant.

*Flower shape.*—Oval and flat in aspect.

*Flower diameter.*—About 5 cm.

*Flower depth* (*height*).—About 4.6 mm.

*Petals.*—Shape: Reniform with emarginate apex and acute base. Quantity, arrangement: 5 petals overlapping. Aspect: Flat. Length: About 2.7 cm. Width: About 2.5 cm. Texture: Smooth, satiny, and glabrous. Margin: Entire. Color: When opening, upper surface: 63A. When opening, lower surface: 63B. Fully opened, upper surface: 63A. Fully opened, lower surface: 63B.

*Peduncle.*—Angle: Erect. Length: About 4.3 cm. Color: 148A.

*Flower bud.*—Shape: Ovoid with spur. Length: About 1.5 cm. Diameter: About 8.5 mm. Color: 55B.

*Spur.*—Shape: Needle-shaped, curved at end. Length: About 5.7 cm. Color: 53A.

*Reproductive organs.*—Androecium: Stamen number: 5. Anther shape: Ovate. Anther size: About 5.8 mm. Anther color: 61B. Pollen color: 8D. Amount of pollen: Abundant. Gynoecium: Pistil length: About 5 mm. Style color: 137A. Stigma color: 138B. Ovary color: 137A.

Disease resistance: No fungal, bacterial nor viral problems observed.

Seed development: Seed production is very rarely observed.

It is claimed:

1. A new and distinct variety of New Guinea impatiens plant named 'Duerihopi', as illustrated and described.

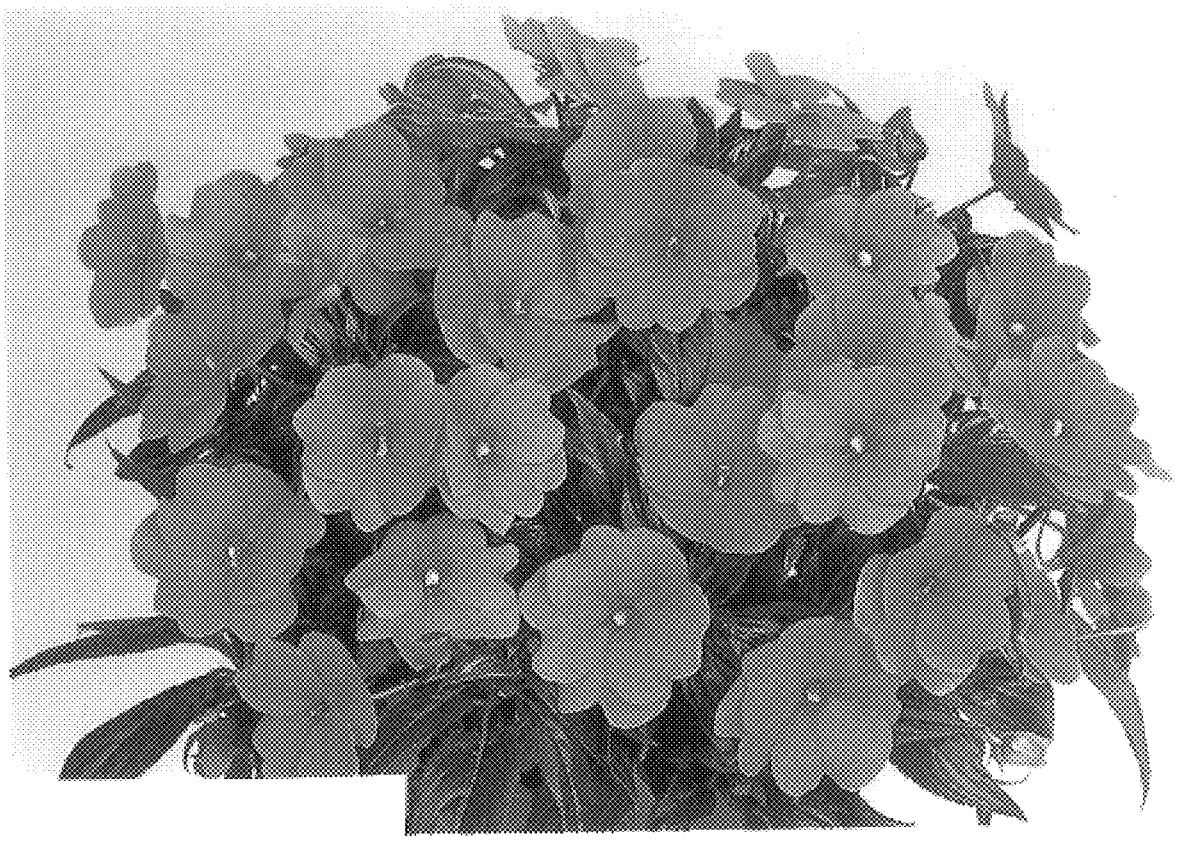

* * * * *